United States Patent [19]

Geoghegan

[11] Patent Number: 5,362,852
[45] Date of Patent: Nov. 8, 1994

[54] MODIFIED PEPTIDE DERIVATIVES CONJUGATED AT 2-HYDROXYETHYLAMINE MOIETIES

[75] Inventor: Kieran F. Geoghegan, Mystic, Conn.

[73] Assignee: Pfizer Inc., New York, N.Y.

[21] Appl. No.: 766,682

[22] Filed: Sep. 27, 1991

[51] Int. Cl.⁵ ........................... C07K 3/08; C07K 7/06
[52] U.S. Cl. ..................................... 530/345; 530/328; 530/405; 530/406; 530/409; 530/410; 534/12
[58] Field of Search ................. 530/345, 391.5, 391.9, 530/405, 406, 409, 410, 328, 351; 435/226; 534/12, 14; 424/1.1, 85.1, 85.2, 94.64, 1.41, 1.45, 1.53, 1.69; 514/2, 12, 15, 21

[56] References Cited

U.S. PATENT DOCUMENTS 4,973,666 11/1990 Eyre .................................... 530/834
5,132,111 7/1992 Vale, Jr. et al. ..................... 530/306

OTHER PUBLICATIONS

Nature, vol. 312, issued 20 Nov. 1984, Lomedico et al., "Cloning and expression fo murine interleukin-1", pp. 458–462.

Eur. J. Biochem., vol. 134, 1983, Maassen et al., "Synthesis and Application of Two Reagents . . . ", pp. 327–330.

*Primary Examiner*—Jeffrey E. Russel
*Attorney, Agent, or Firm*—Peter C. Richardson; Paul H. Ginsburg; Robert F. Sheyka

[57] ABSTRACT

A process is disclosed for site-directed chemical modification of peptides and proteins that consists of two steps; (a) selective oxidation of a 2-hydroxyethylamine moiety, —CH(NH$_2$)—CH(OH)—, in the peptide or protein to generate an aidehyde, and (b) reaction of the new aldehyde with a second reagent to form a product in which the native biological properties of the peptide are augmented by new and useful properties conferred by the second reagent. Additionally, the invention pertains to certain specified types of product formed by the above process.

11 Claims, 7 Drawing Sheets

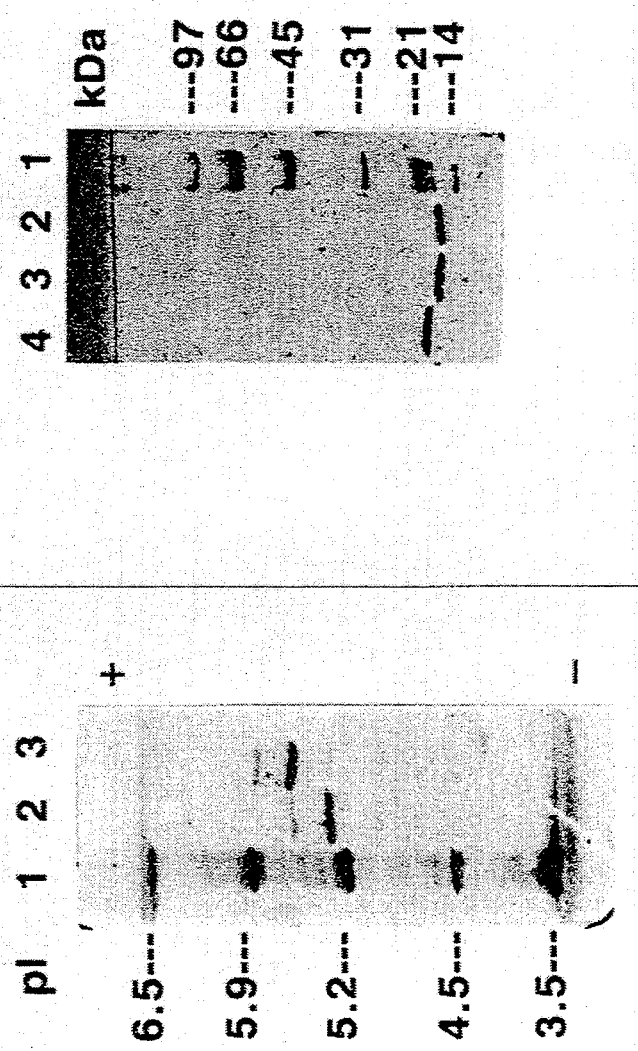
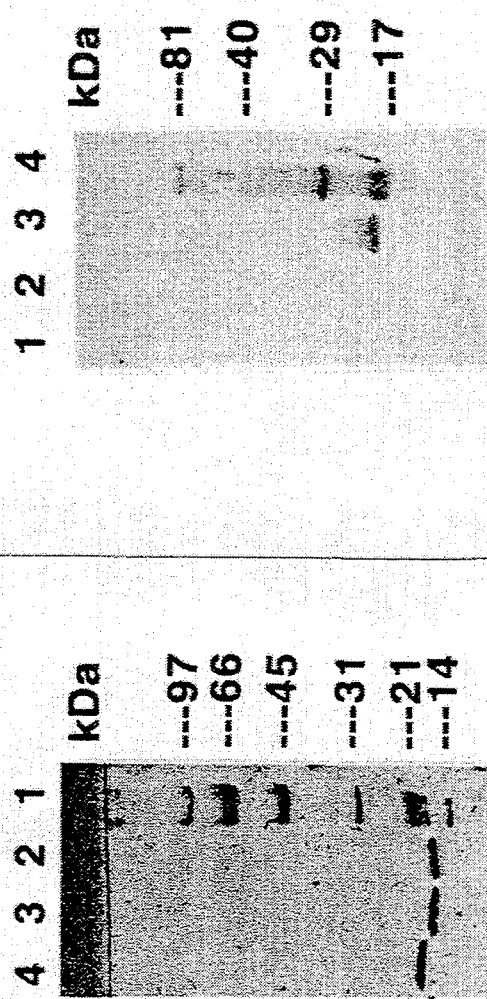
FIG. 3A  FIG. 3B  FIG. 3C

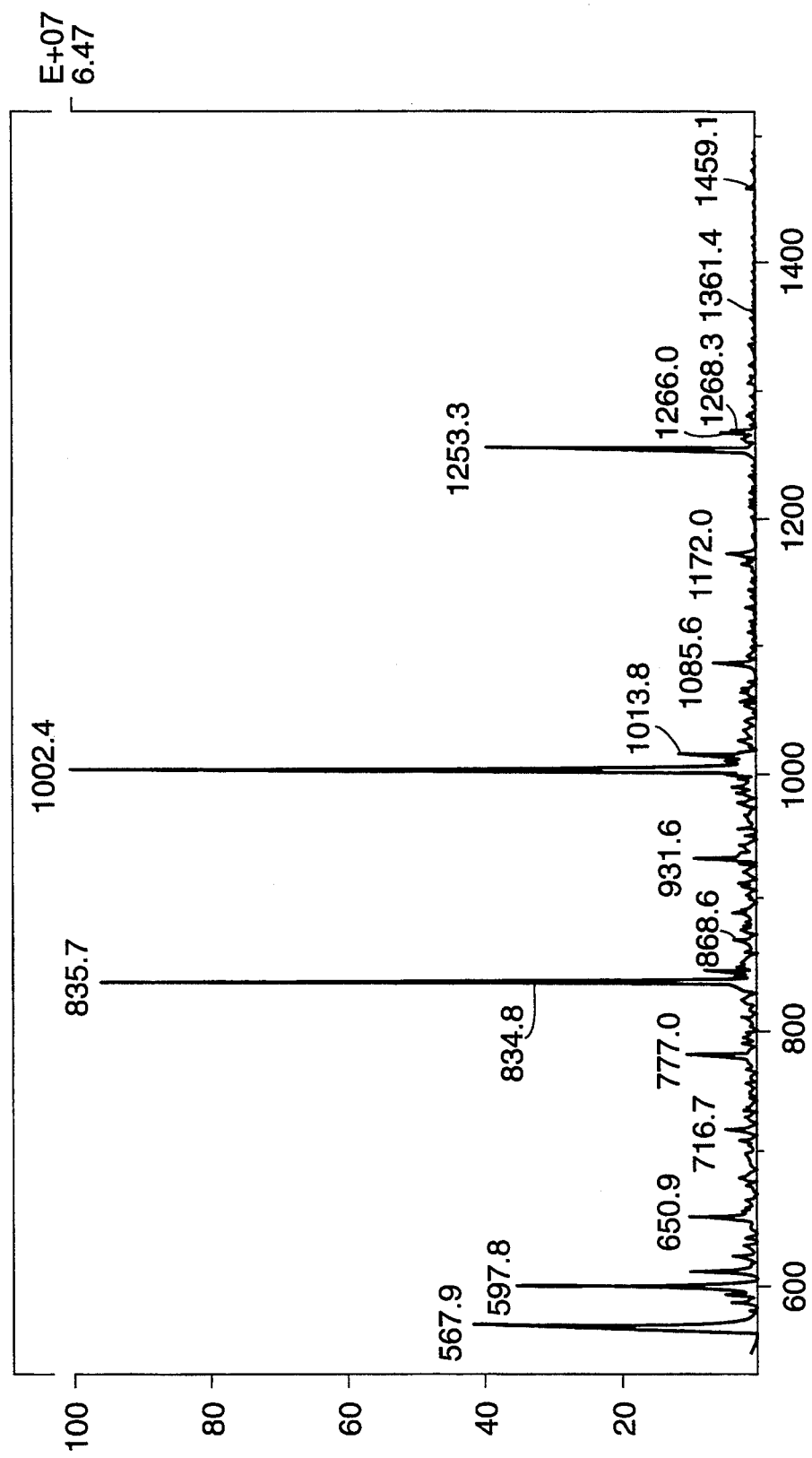

MODIFIED PEPTIDE DERIVATIVES CONJUGATED AT 2-HYDROXYETHYLAMINE MOIETIES

BACKGROUND OF THE INVENTION

In biochemical research and biotechnology, it is often desirable to couple another molecule to a peptide in order to generate a product with novel properties. This involves modifying a peptide in such a manner that it retains its original biospecific function (e.g. the ability to bind to a receptor) but gains, in addition, a new property. Such derivatized peptides may be called peptide conjugates.

Peptide conjugates have a range of current and potential applications. Non-limiting examples include their use in studies of receptor binding and in the isolation of receptors; in biophysical studies of protein three-dimensional structure and mobility; in many types of diagnostic procedures; in the raising of anti-peptide antibodies and in affinity chromatography. Peptide conjugates may also be used in the generation of synthetic enzymes (through the strategic placement of nonpeptide cofactors in peptide chains), and in such direct biomedical applications as tumor imaging and targeted drug delivery. In the latter areas, peptides that are specifically recognized by particular cell types (e.g. malignant tumor cells) may be used as targeting devices that deliver imaging agents or cell-killing drugs to the desired sites in the body.

Peptides are multifunctional organic molecules that possess a range of potentially reactive groups. These include amino groups (one at the amino terminus, others on the side chains of lysyl residues), carboxyl groups (one at the carboxy terminus, others on side chains of glutamyl and aspartyl residues), as well as others including phenol (tyrosine), imidazole (histidine), guanidino (arginine) and indole (tryptophan) groups. An exemplary peptide conjugate formation involves introducing a biotin moiety into a peptide in order to facilitate its detection and quantitation through the strong and specific recognition of biotin by the protein avidin. (Biotin is a small water-soluble vitamin; avidin can be endowed with many properties that facilitate its quantitation, allowing it to serve as the basis of an indirect assay for the biotinylated peptide).

Biotin is an example of a "tagging" group that allows a peptide to be recognized and specifically bound; other groups, known as "reporter groups", may allow information concerning the location and disposition of the peptide to be ascertained directly without the need of an intervening second agent. Biotin is used as an example in the following discussion, but represents any nonpeptide tag or reporter group which might be coupled to a protein or peptide.

Current technology allows the introduction of biotin at a selected type of target site by using a group-specific reagent, i.e. a modified form of biotin designed to react with a selected class of groups on the peptide. For example, in N-hydroxysuccinimidobiotin, biotin is attached to a reactive entity that readily couples to amino groups. The problem with this approach is that the reagent can react with any of the amino groups present in the peptide or protein, giving (in most cases) a mixture of products. One then is left with the unpleasant choice of performing experiments with a heterogeneous preparation that contains a number of different modified peptides, or of fractionating the mixture of products and characterizing each product to identify the site(s) of modification. Each alternative has evident drawbacks. Thus, reagents that are group-specific for target sites normally present in proteins and peptides can give a unique product only in the minority of instances in which the peptide contains just one of the groups to which the reagent is directed.

Another approach has been site-directed modification. As knowledge of protein and peptide structure improves, scientists increasingly understand the relative contributions to biological activity made by particular regions of a protein. For example, it may be known that some part of a protein is unimportant for the biological activity of the protein. If this protein is being conjugated to a non-peptide group, it would be desirable to be able to direct the incoming modifying group to a site in the protein that is not biologically essential. This would greatly increase the probability of the conjugate retaining the native biological properties of the original peptide while also acquiring the new properties conferred by the label. In addition, a single product would be formed, making purification and characterization of the conjugate relatively simple.

Using conventional approaches, such a result could be expected to be achieved only in the minority of cases in which a single group of the type targeted with a group-specific reagent (e.g. an amino group) exists in the region of the peptide selected to receive the modification, while no other group of the same type exists anywhere in the peptide.

Thus, new strategies are required that allow peptides to be modified at unique and preselected locations. A discussion of the need for such technology was given recently in the particular case of biotinylation:

"An effective method has yet to be reported for the selective incorporation of a single biotin molecule into proteins at a predetermined site. The biotin-containing labeling reagents described in . . . this volume are all group specific; such residue-specific biotinylation would therefore be contingent on the presence of a single modifiable group in the desired target protein. Likewise, the selective modification of C- or N-terminal amino acids is also complicated by the presence of aspartic and glutamic acids and lysines in proteins."

A. Schwarz, C. Wandrey, E. A. Bayer, and M. Wilchek (1990) Methods Enzymol. 184, 160–162.

These authors demonstrated an approach that allows biotin to be introduced selectively at the C-terminus of a peptide or protein by an enzymatic procedure.

A second recent discussion of the issue was given by J. W. Drijfhout et al.:

"Synthetic peptides play an important role in current biochemical, pharmacological, and immunological research and are widely prepared using solid-phase methodology. After deprotection and cleavage from the solid support, further processing of the peptides is often required, for example, coupling with marker substances (labels) or proteins. Numerous homo- and heterobifunctional-crosslinking reagents have been used for such purposes. However, it is often difficult to achieve selectivity in the coupling reaction since most peptides contain several reactive groups."

J. W. Drijfhout, W. Bloemhoff, J. T. Poolman and P. Hoogerhout (1990) Anal. Biochem. 187, 349–354.

These authors proposed a solution to the problem in which the N-terminus of synthetic peptides is modified with a group that contains a chemically masked sulfhydryl (—SH) group. At the appropriate time, the —SH group is unmasked and allowed to react with a modifying label which is thereby located at the N-terminus of the peptide.

This information reflects the concern and interest of peptide chemists that a method be defined which will allow a group with useful properties to be added to a peptide at a single, precisely known site. Unlike the methods noted above, such a site should preferably not be limited to the N- or C-terminus of a peptide; ideally, the unique coupling site should be anywhere in a peptide that the chemist chooses. Thus the present invention is directed to a method that meets many of the requirements expressed in the extracts given above from current literature.

BRIEF DESCRIPTION OF THE DRAWINGS

FIGS. 3A–C shows coupling of 6-((biotinoyl)amino)-caproic acid hydrazide to interleukin-1α.

FIGS. 4A–B shows electrospray mass spectrometry of a CRF conjugate.

SUMMARY OF THE INVENTION

Figure 1A:
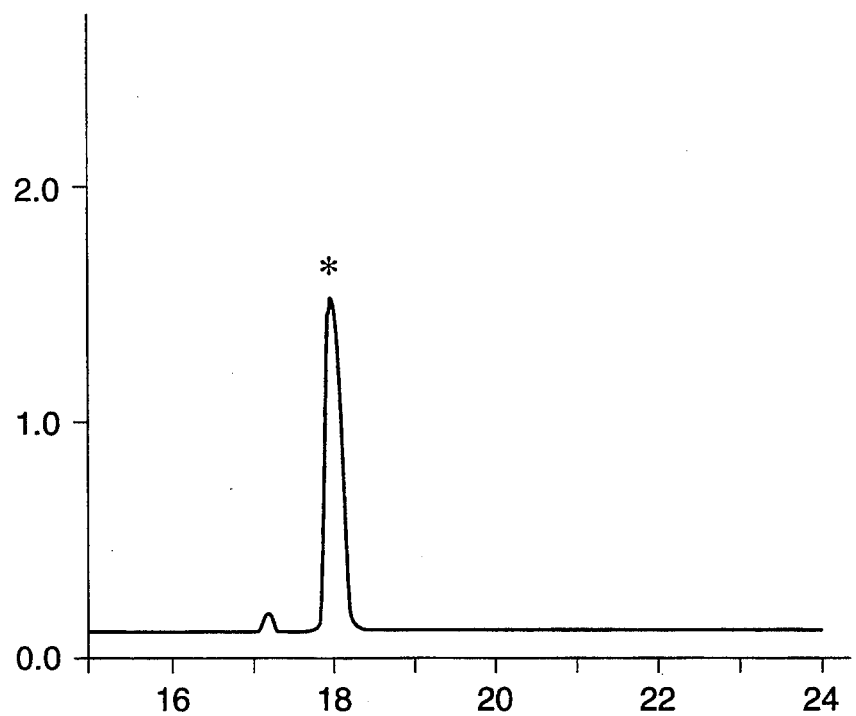
FIG. 1a shows the high pressure liquid chromatography peak of Ser-Tyr-Ser-Met-Glu-His-Phe-Arg-Trp-Gly (SEQ. ID. NO: 1).

In one embodiment, the present invention is directed to a process for the conjugation of a group with useful functional properties to a peptide comprising (a) generating an aldehyde by oxidation of a 2-hydroxyethylamine structure, said 2-hydroxyethylamine structure either naturally occurring or inserted in said peptide;

(b) reacting a suitable reagent containing a group with useful functional properties with said aldehyde generated in step (a).

Preferred is the process wherein the reagent is a hydrazide.

Especially preferred is the process wherein the oxidation of step (a) is periodate oxidation.

Also especially preferred is the process wherein said 2-hydroxyethylamine structure occurs as part of a serine or threonine amino terminus of a peptide.

Also preferred is the process wherein said 2-hydroxyethylamine structure occurs as part of a serine or threonine residue present at the amino terminus of a synthetic peptide.

Also especially preferred is the process wherein said 2-hydroxyethylamine structure occurs as part of a serine or threonine residue present at the amino terminus of a peptide as a result of genetic manipulation on enzymatic treatment.

Also preferred is the process wherein said 2-hydroxyethylamine structure occurs naturally as part of a hydroxylysine residue or wherein said 2-hydroxyethylamine structure is part of a hydroxylysine residue which is inserted into a synthetic peptide.

Also especially preferred is the process wherein said functional group is biotin, lucifer yellow, a chromophore, a fluorescent label, or contains a radionuclide.

Also preferred is the process wherein said peptide is the amino-terminal decapeptide of human adrenocorticotropin, said decapeptide having the sequence Ser-Tyr-Ser-Met-Glu-His-Phe-Arg-Trp-Gly (SEQ. ID NO:1).

Also especially preferred is the process wherein said serine residue is found at the amino terminus of cytokines, preferably interleukin-1α and interleukin-8.

Also especially preferred is the process wherein said serine residue is found at the amino terminus of corticotropin releasing factor.

In another embodiment the present invention is directed to a peptide conjugate of the formula R—NH—N=CH—C-Tyr-Ser-Met-Glu-His-Phe-Arg-Trp-Gly; (SEQ. ID. NO:2) =CH—CO— represents the oxidized form of the amino terminal Ser, and R is a group with useful functional properties.

In another embodiment, the present invention is directed to a peptide conjugate of the formula R—NH—N=CH—CO-IL-1α wherein R is a group with useful functional properties, =CH—CO represents the oxidized form of the amino terminal Ser and IL-1α is the rest of the peptide structure of interleukin-1α.

In another embodiment, the invention is directed to a peptide conjugate of the formula R—NH—N=CH—CO—CRF wherein R is a group with useful functional properties, =CH—CO-represents the oxidized form of the amino terminal Ser and CRF is the rest of the peptide structure of corticotropin releasing factor.

In another embodiment, the present invention is directed to a peptide conjugate having the structure R—NH—N=CH—CO—X wherein R is a group with useful functional properties and X is the remainder of the peptide structure following the modified amino terminus.

In another embodiment, the present invention is directed to a peptide conjugate having the structure P1—NH—CH[—CH$_2$—CH$_2$—CH=N—NH—R—]—CO—P2 wherein R is a group with useful functional properties and P1 and P2 respectively represent the remainder of the peptide sequence of the amino terminus and carboxy terminus respectively.

DETAILED DISCUSSION OF THE INVENTION

To achieve single-site (site-directed) labeling of a peptide, it is necessary that the peptide contain a single, uniquely sited group at which the incoming label reacts to form a stable conjugate. As discussed above, this group should be of a kind not ordinarily represented in the peptide. This strategy allows peptides destined for tagging with a reporter group to possess all their normal complement of amino acid side chains along with free N- and C-termini, and thus retain all the elements of structure required for full biological activity. Hereinafter, the term "group with useful functional properties" will be used to describe these reporter groups, tagging groups, etc.

The process of the present invention comprises generating a single aldehyde group in the peptide at a known site by, for example, periodate oxidation of a 2L-hydroxyethylamine structure R—CH(NH$_2$)—CH(OH)—R'. Such structures exist in proteins only in two cases: (i) where the N-terminus is Ser(R'=H; R=peptide chain beginning from peptide carbonyl carbon of N-terminal Ser residue) or Thr (R'=CH₃, R=peptide chain beginning from peptide carbonyl carbon of N-terminal Thr residue); (ii) when a residue of hydroxylysine is present (R=H; R'=peptide chain beginning with γ-carbon of hydroxylysine residue); hydroxylysine occurs naturally only in collagen, but can be inserted anywhere in a synthetic peptide.

Second, a suitable reagent is allowed to react with the aldehyde group. A non-limiting example of the type of reagent that may be used is a hydrazide reagent (R''—NH—NH₂), which may be coupled to the new aldehyde. The resulting hydrazone conjugate (R''—NH—N=CH—CO-peptide) is stable and suitable for use in biochemical experiments. The process as applied to modification of a peptide at its N-terminus may be summarized as follows:

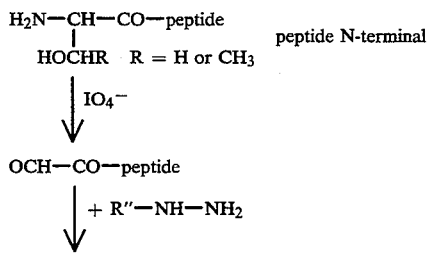

The process as applied to modification of a peptide at a hydroxylysine residue may be summarized as follows:

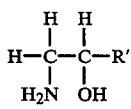

R' = remainder of peptide structure beginning with γ-carbon of hydroxylysine side chain

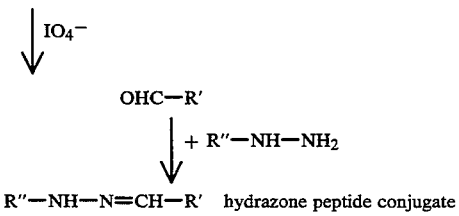

The process may be used on any peptide with the required structural features. A relatively simple peptide may be tagged with a group such as, for example, biotin. The process may also be applied to modifying larger proteins, for example, of 18 kDa or larger. The process may be applied to modify peptide hormones, with the modified peptide binding to its cognate receptor with undiminished affinity compared to the peptide as naturally isolated. The results illustrate that a peptide conjugate of the new type can interact successfully with biological receptors.

Having described the invention in general terms, reference is now made to specific examples. It is to be understood that these examples do not limit the present invention, the scope of which is determined by the appended claims.

EXAMPLE 1

Ser-Tyr-Ser-Met-Glu-His-Phe-Arg-Trp-Gly (SEQ ID NO:1)

Using the one-letter code for the amino acids, the peptide Ser-Tyr-Ser-Met-Glu-His-Phe-Arg-Trp-Gly (SEQ ID NO:1) is denoted Ser-Tyr-Ser-Met-Glu-His-Phe-Arg-Trp-Gly (SEQ ID NO: 1). This peptide corresponds to the N-terminal decapeptide of the human form of the peptide hormone adrenocorticotropin. Ser-Tyr-Ser-Met-Glu-His-Phe-Arg-Trp-Gly (SEQ ID NO: 1) was chosen for initial studies because it possesses several potentially periodate-sensitive sites in addition to the N-terminal seryl residue; these are the Met, Tyr, Trp and His residues. For the strategy described here to be successful, it is mandatory that periodate react with sufficient selectivity at the desired target site, leaving the rest of the peptide essentially free of oxidative side reactions. Because the peptide contained the most likely side reaction sites, the challenge of modifying Ser-Tyr-Ser-Met-Glu-His-Phe-Arg-Trp-Gly (SEQ ID NO: 1) without causing extensive side reactions represented an excellent test of the viability of the new method.

In preliminary studies, it was noted that optimal selectivity for modification of the N-terminal Ser is achieved when the periodate step is performed at pH 7.0 using no more than a 1–2 fold excess of periodate over peptide. This result agreed with published reports that the desired reaction of periodate with the 2-hydroxyethylamine structure (as found in N-terminal Ser) is far faster than competing reactions, so that use of a low molar ratio of periodate results in the oxidant being rapidly consumed by the desired reaction (for a review, see H. B. F. Dixon (1984) J. Prot. Chem, 3, 99–108).

Figure 1B:
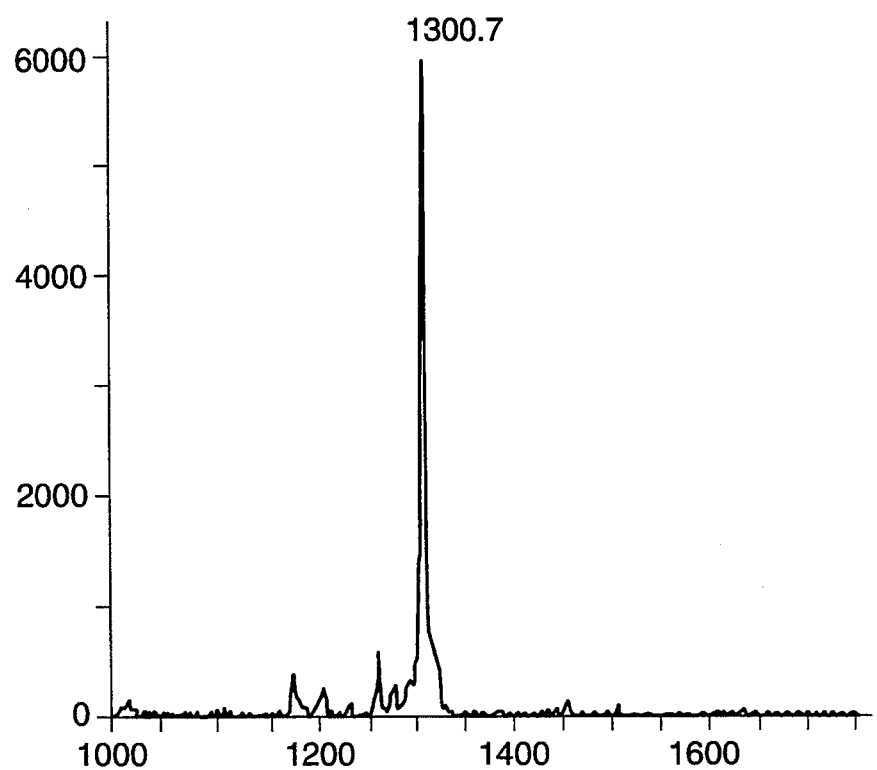
FIG. 1b shows the plasma desorption mass spectrometry of Ser-Tyr-Ser-Met-Glu-His-Phe-Arg-Trp-Gly (SEQ. ID. NO: 1).

Ser-Tyr-Ser-Met-Glu-His-Phe-Arg-Trp-Gly (SEQ ID NO: 1) from a commercial source (Sigma) was shown by reversed-phase high-pressure liquid chromatography (HPLC) performed using a Vydac C4 column (FIG. 1a) to consist of a single major component with only trace impurities. Chromatography was based on differential elution of components in a gradient of increasing acetonitrile concentration in the presence of 0.1% trifluoroacetic acid. The major component (the peak marked with an asterisk in FIG. 1a) was collected from the HPLC and shown by plasma desorption mass spectrometry (PDMS) (FIG. 1b) to have the molecular weight expected for Ser-Tyr-Ser-Met-Glu-His-Phe-Arg-Trp-Gly (SEQ ID NO: 1). In detail, the predicted molecular weight for Ser-Tyr-Ser-Met-Glu-His-Phe-Arg-Trp-Gly (SEQ ID NO: 1) was 1299.4; the observed value for the molecular ion (MH+) of 1300.7 was in excellent agreement with this, and confirmed the authenticity of the Ser-Tyr-Ser-Met-Glu-His-Phe-Arg-Trp-Gly (SEQ ID NO: 1). For future reference, it is noted that PDMS operates with a mass accuracy of approximately 0.2%.

Figure 1C:
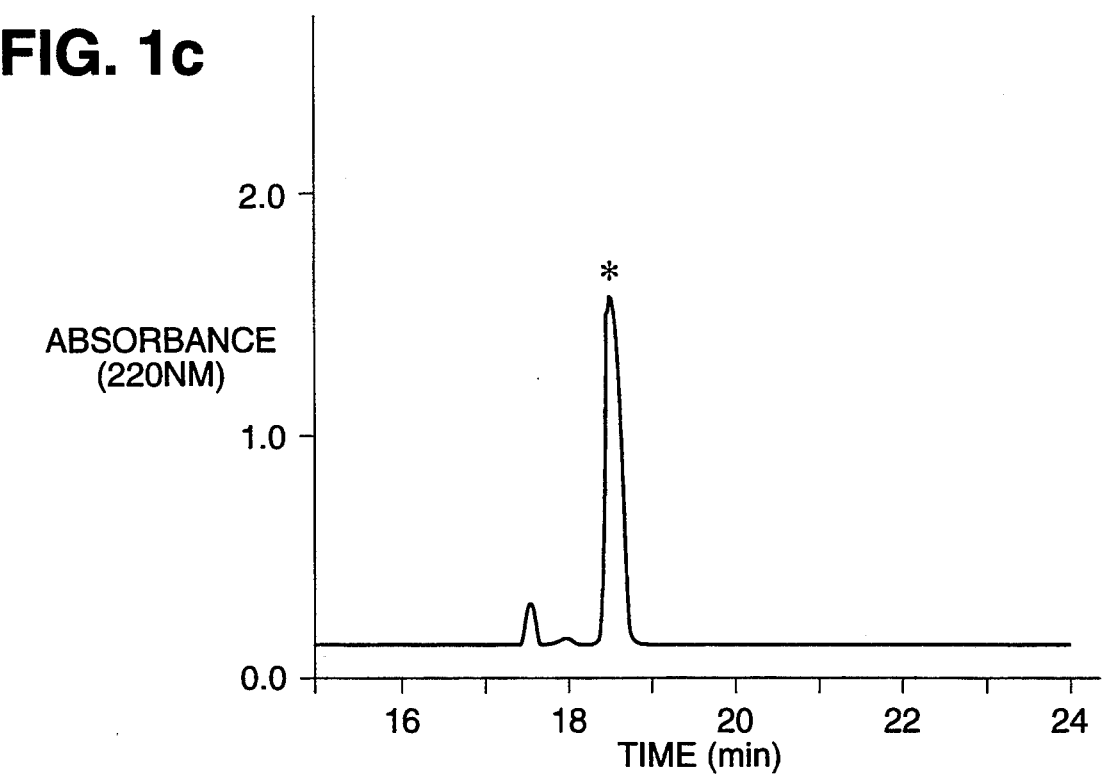
FIG. 1c shows the high pressure liquid chromatography fractionation of the oxidized form of Tyr-Ser-Met-Glu-His-Phe-Arg-Trp-Gly (SEQ ID NO: 2).
Figure 1D:
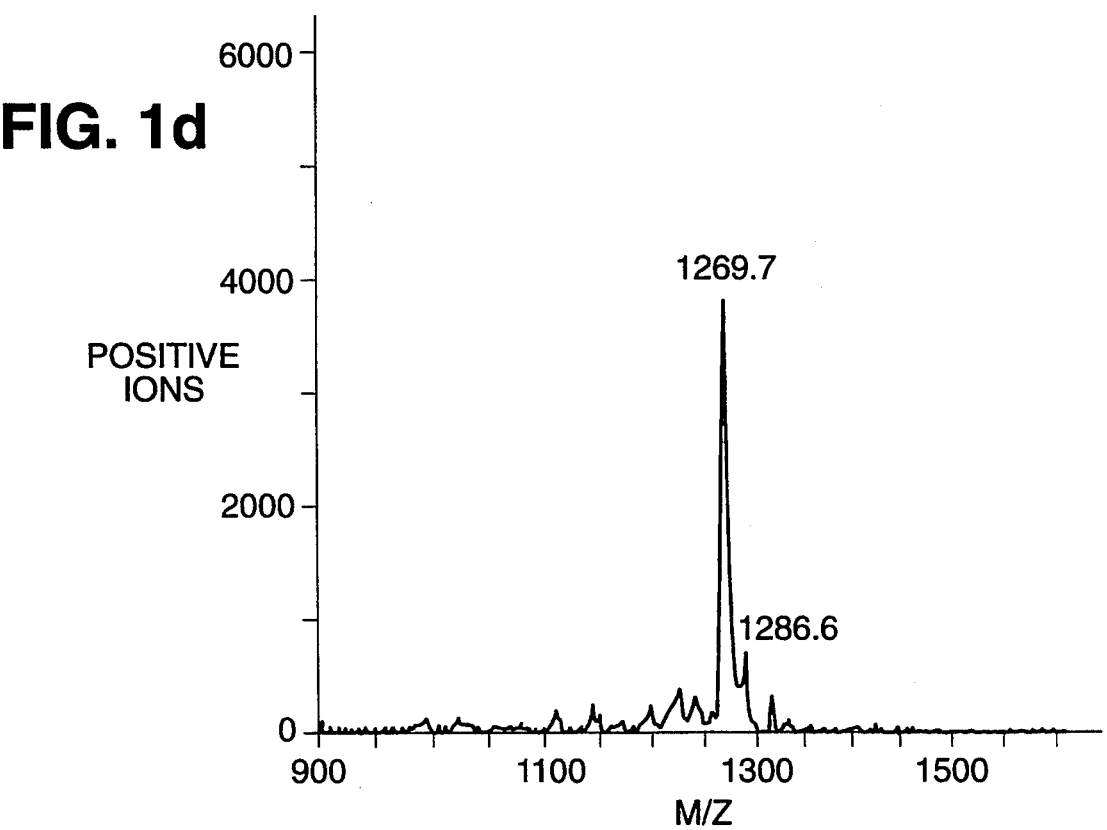
FIG. 1d shows the plasma desorption mass spectrometry peak of OHC-CO-Tyr-Ser-Met-Glu-His-Phe-Arg-Trp-Gly (SEQUENCE ID NO: 2).

In a typical experiment, Ser-Tyr-Ser-Met-Glu-His-Phe-Arg-Trp-Gly (SEQ ID NO: 1) (0.20 mM) was allowed to react in sodium phosphate buffer (0.03M, pH 7.0) with sodium periodate (0.22 mM) for 4 minutes at 21° C. After this, the reaction mixture was fractionated by HPLC (FIG. 1c). The desired product, namely glyoxylyl-Tyr-Ser-Met-Glu-His-Phe-Arg-Trp-Gly (SEQ ID NO: 2) (OHC—CO-Tyr-Ser-Met-Glu-His-Phe-Arg-Trp-Gly) (SEQ ID NO: 2), was shown by PDMS to account for >95% of the products recovered (FIG. 1d); this result demonstrated the selective nature of the action of periodate upon the peptide. The double peak observed in the PDMS spectrum reflected the presence of two forms of the oxidized peptide, these being due to the unhydrated and hydrated forms of the aldehyde which was created by the oxidative reaction.

Figure 2A:
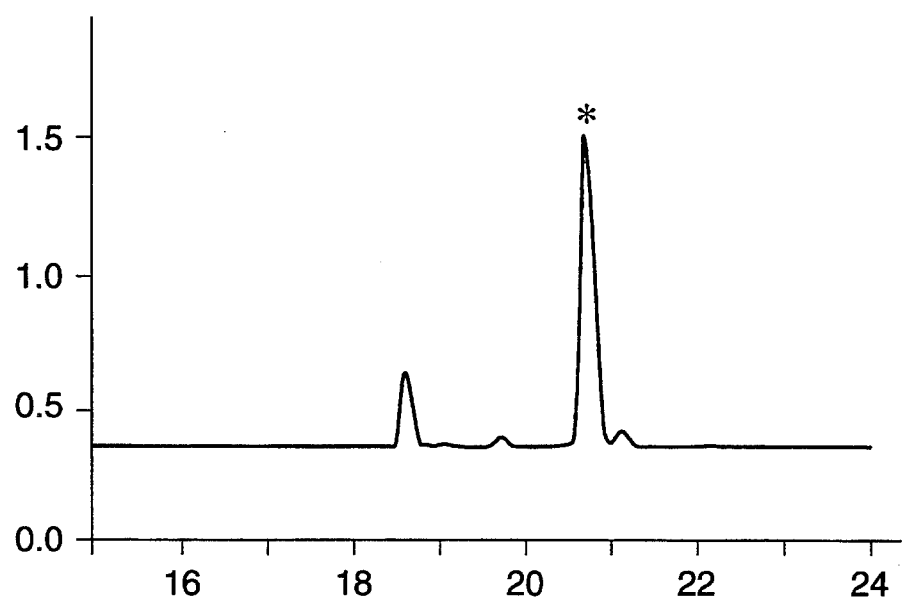
FIGS. 2A–D shows coupling of two hydrazide reagents to the oxidized form of Ser-Tyr-Ser-Met-Glu-His-Phe-Arg-Trp-Gly (SEQ ID NO: 1).
Figure 2B:
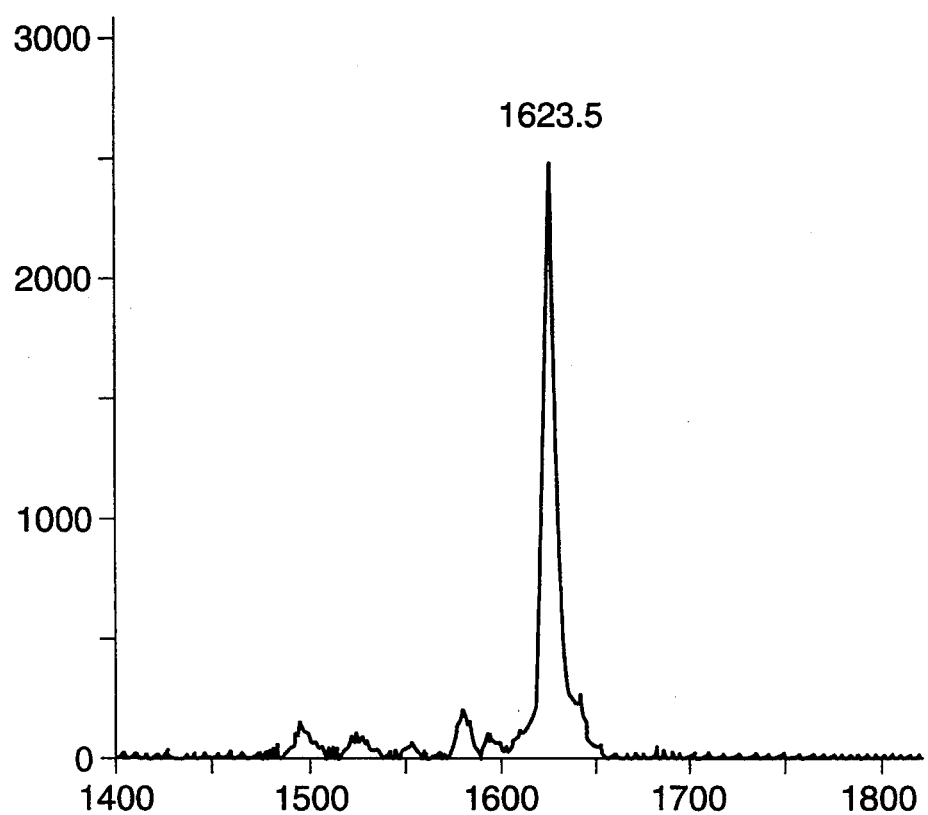
Figure 2C:
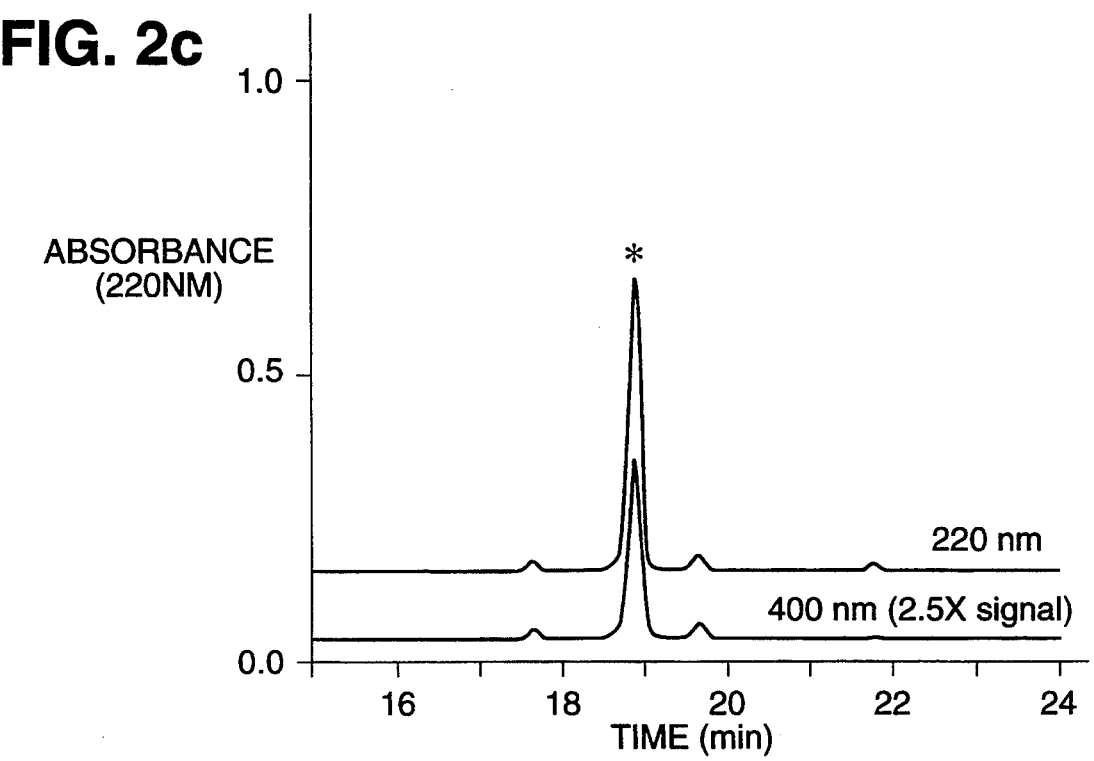

Aliquots of the peak fraction containing the desired product were dried by centrifugal concentration, and were then allowed to react with a hydrazide reagent. In two examples, OHC—CO-Tyr-Ser-Met-Glu-His-Phe-Arg-Trp-Gly (SEQ ID NO: 2) (0.22 mM) was allowed to react with, respectively: 6-((biotinoyl)amino)caproic acid hydrazide (henceforth, biotin-X-hydrazide) (16 mM in 0.04M sodium acetate, pH 4.5, containing 22% acetonitrile); and Lucifer Yellow (12.5 mM in 0.025M sodium acetate, pH 4.5). The reactions (50 μl each) were allowed to proceed for 135 minutes at 37° C., after which 170 μl of 0.05M Na phosphate buffer, pH 7.0, was added, and the incubates were fractionated by the HPLC procedure described above (FIG. 2a and 2c).

Figure 2D:
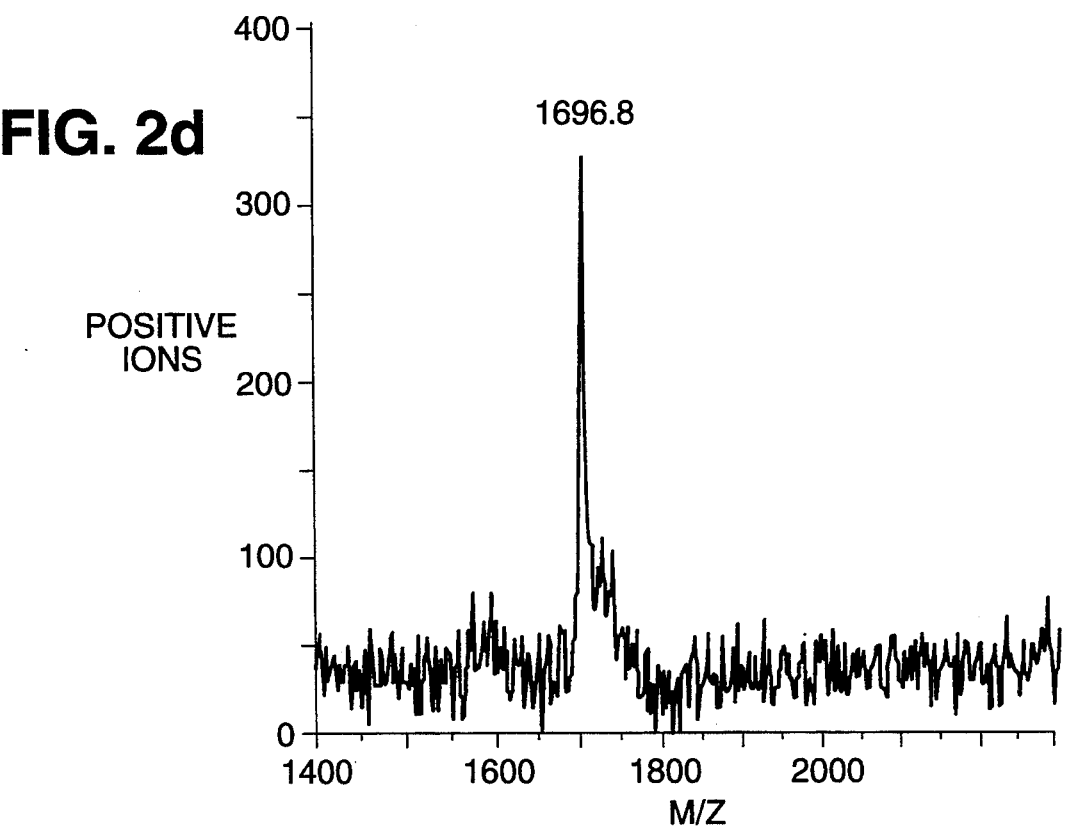

The new products recovered were characterized by plasma desorption mass spectrometry. In each case, the observed mass of the purified product confirmed that it was the desired hydrazone adduct of biotin-X-hydrazide (FIG. 2b) or Lucifer Yellow (FIG. 2d) with OH-C—CO-Tyr-Ser-Met-Glu-His-Phe-Arg-Trp-Gly (SEQ ID NO: 2). The results confirmed the viability (in chemical terms) of the proposed new strategy for designing and preparing peptide conjugates. A ten amino acid fragment of human adrenocorticotropin had been furnished either with (i) a biotin moiety (useful to permit detection or isolation of the conjugate by application of powerful and flexible avidin-biotin technology, well known to those skilled in the art of protein and peptide chemistry); or (ii) a strongly chromophoric and fluorescent label, useful for allowing detection of the peptide and following its interactions with other biological molecules. The results represented an invention capable of being applied to any peptide possessing the required elements of structure as detailed above.

EXAMPLE 2

Interleukin-1α

As a further exercise of the invention, the method was applied to a comparatively large protein target. Interleukin-1α is an important cytokine which plays a critical role in the human body's response to disease and tissue damage. It is also implicated in the underlying pathology of disease states which result in undue inflammatory responses, such as arthritis. As such, the protein is an important subject of research, and new technology to facilitate analysis of its functional properties is of considerable value.

In the experiment, interleukin-1α was tagged with a fluorescent label or biotin attached at a specific point in its structure. This facilitated tracking the protein through the course of its action as a hormone that influences the behavior of cells involved in the inflammatory response. Using the murine form of the protein (molecular weight of 17,991), which has a Ser residue at its N-terminus (SEQ ID NO: 3), interleukin-1α was tagged selectively at the N-terminus with biotin-X-hydrazide. To begin the procedure, interleukin-1α (14 μM) was allowed to react with sodium periodate (40 μM, i.e. a 3:1 molar ratio of oxidant to protein). Periodate oxidation of the N-terminus caused a positively charged site on the protein (the N-terminal amino group) to be replaced by an uncharged aldehyde function, so that it was possible to follow the reaction by isoelectric focussing (FIG. 3a). The result showed that the protein was quantitatively converted by the oxidation to a more anodic form, consistent with the desired oxidation having proceeded to completion with a high degree of selectivity. (Key to Figure: lane 2, interleukin-1α before oxidation; lane 3, interleukin-1α after oxidation.)

The oxidized protein was allowed to react with biotin-X-hydrazide (8mM in 25% acetonitrile/0.05M sodium acetate, pH 4.5) at 22 C for 16 hours. To remove the excess coupling reagent, the reaction mixture (0.44 ml) was then gel filtered using a Pharmacia Fast Desalting Column HR 10/10 equilibrated with 0.02M Tris HCl, pH 7.0.

Proceeding with final recovery of the product, the protein fraction from this procedure was subjected to anion-exchange chromatography using a Pharmacia MonoQ HR 5/5 anion-exchange column operating at a flow rate of 1 ml/min. A sodium chloride gradient in 0.02M Tris HCl was used to elute bound protein, and the biotinylated interleukin-1α was eluted as a sharp peak at about 0.1M NaCl in the gradient which accounted for >80% of the total protein eluted (as gauged by absorbance at 280 nm). The modified protein was characterized by SDS-polyacrylamide gel electrophoresis (FIG. 3b), in which the oxidized and biotinylated protein (Lane 4) migrated less rapidly than control samples (Lanes 2, 3) which had not received biotin by a factor consistent with incorporation of the 371 Da biotin-X-hydrazide. In a further proof of structure, a similar electrophoretic gel was electroblotted to a polyvinylidenedifluoride membrane and probed for the presence of biotin using a conjugate of avidin with horseradish peroxidase. Only the protein subjected both to oxidation and biotinylation (FIG. 3c, lane 3) was detected by this procedure; the control samples of murine interleukin-1α (Lanes 1, 2) were not detected. This result showed that biotin had been incorporated specifically by means of the site-directed chemistry employed.

Site-directed biotinylation of interleukin-1α creates a useful new reagent for biochemical and cellular research. For example, the new conjugate has been used to permit fluorescence-activated cell sorting of cells which express the interleukin-1 receptor on their surfaces. This was done by allowing the biotinylated cytokine to bind to its receptor on the cell surface, after which a fluorescent form of avidin was allowed to bind to the cell-bound interleukin-1. As a consequence, cells to which the biotinylated probe had bound were rendered fluorescent and capable of being sorted from cells which were not so selected.

EXAMPLE 3

Corticotropin Releasing Factor

Corticotropin releasing factor (CRF) is a peptide hormone thought to be critically important in the pathology of certain types of anxiety and depression. As such, it is the subject of much current research, especially studies centered on its interaction with its receptor.

To develop modified forms of CRF, the ovine form of the peptide (which has N-terminal Ser) was selected. The ovine peptide binds well to the human CRF receptor. In addition, as this peptide is notoriously prone to oxidation of its sole Met residue, the form of the peptide used was that in which the Met exists as the sulfoxide form (CRF [Met$^{21}$O]).

Figure 4B:
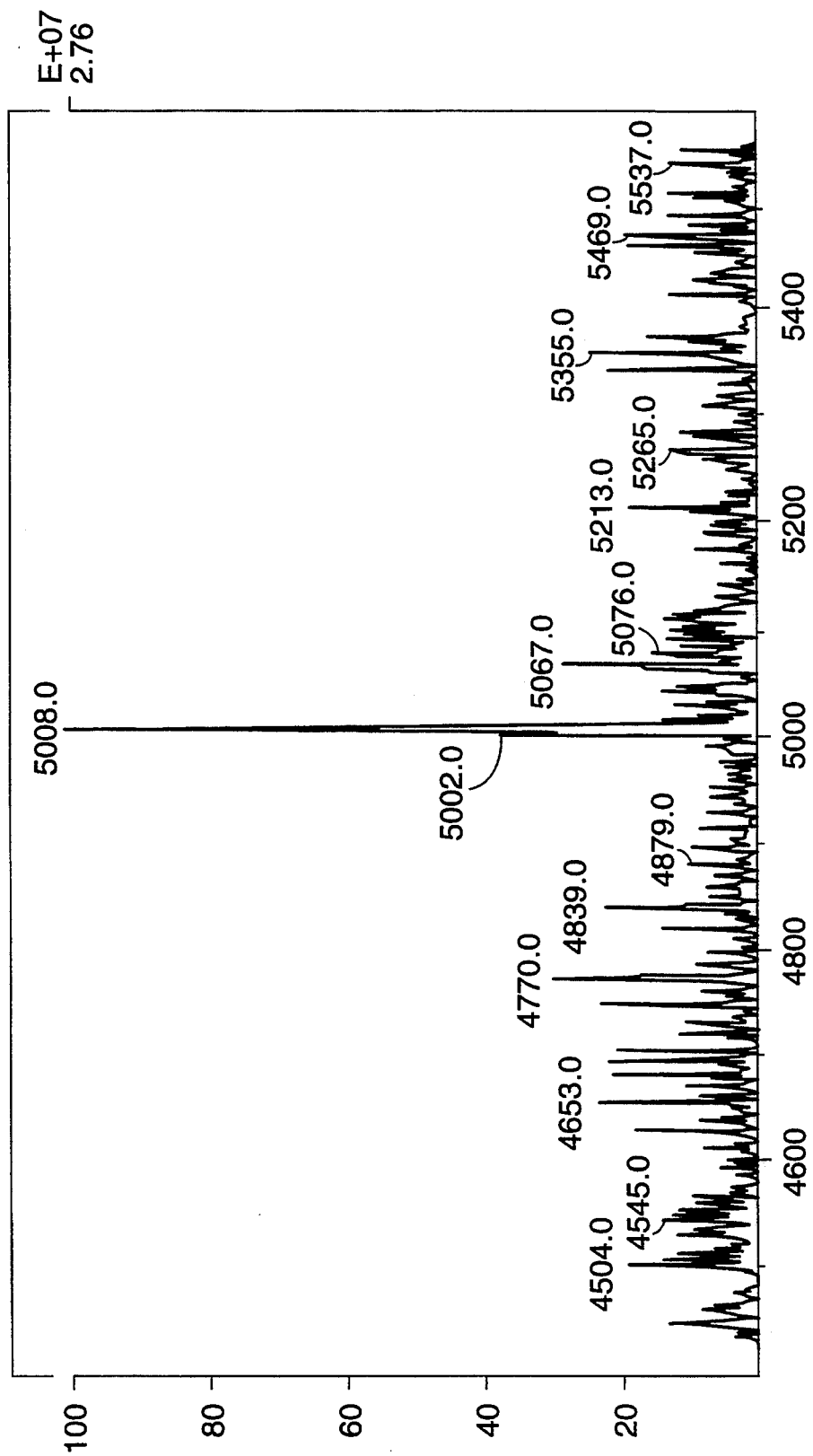

To oxidize the N-terminal Ser of CRF, the peptide (0.19 mM) was allowed to react with sodium periodate (0.29 mM) in the presence of 0.035M sodium phosphate buffer pH 7.0 at room temperature for 4 minutes. The reaction mixture was then fractionated by reversed-phase HPLC as above, and the oxidized peptide was collected and its structure was verified to be as predicted by PDMS. After drying, the peptide was coupled in separate reactions as described above to biotin-X-hydrazide and Lucifer Yellow. The products were isolated by HPLC and, as for hydrazone adducts formed with Ser-Tyr-Ser-Met-Glu-His-Phe-Arg-Trp-Gly-(SEQ ID NO: 1), their identity was verified by mass spectrometry. FIG. 4 shows the delineation by electrospray mass spectrometry of the mass of N-terminally biotinylated ovine CRF [Met$^{21}$O] (SEQ ID NO:4). As biotin-X-hydrazide has a mass of 371, the observed mass of the conjugate of 5008 is in precise agreement with prediction for the desired material.

The products were dissolved in 0.05M sodium phosphate, pH 7.0, and tested for their ability to bind to the human CRF receptor (prepared from cultured SK-N-SH cells). $IC_{50}$ values in the region of 5 nM were obtained for both conjugates; as underivatized CRF [Met$^{21}$O] also gave 5 nM, the results indicated that derivatization with the tagging groups did not disrupt receptor binding.

Projected uses of the tagged forms of CRF include detection of recombinant-derived expression of the CRF receptor in the course of expression cloning of that molecule, and applications in fluorescence-activated cell sorting.

In addition to hydrazide reagents, other non-limiting examples of reagents that may usefully be reacted with the aldehyde generated by the oxidative step include (I) amines, which when added in the presence of a suitable reducing agent, can be conjugated to the peptide by reductive amination; (II) O-substituted derivatives of hydroxylamine, which can be conjugated to the peptide to give oximes; and (III) reducing agents such as borohydride and cyanoborohydride which, if used in tritiated form, can be used to radiolabel the peptide by reducing the aldehyde group to an alcohol with stable incorporation of tritium.

---

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Ser  Tyr  Ser  Met  Glu  His  Phe  Arg  Trp  Gly
1               5                         10
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Tyr  Ser  Met  Glu  His  Phe  Arg  Trp  Gly
1                    5
```

( 2 ) INFORMATION FOR SEQ ID NO:3:

( i ) SEQUENCE CHARACTERISTICS:
        ( A ) LENGTH: 156 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Ser  Ala  Pro  Tyr  Thr  Tyr  Gln  Ser  Asp  Leu  Arg  Tyr  Lys  Leu  Met  Lys
1                   5                        10                       15

Leu  Val  Arg  Gln  Lys  Phe  Val  Met  Asn  Asp  Ser  Leu  Asn  Gln  Thr  Ile
                    20                       25                       30
```

| | | | | | | | | | | | | | | |
|---|---|---|---|---|---|---|---|---|---|---|---|---|---|---|
|Tyr|Gln|Asp<br>35|Val|Asp|Lys|His|Tyr<br>40|Leu|Ser|Thr|Thr|Trp<br>45|Leu|Asn|Asp|
|Leu|Gln<br>50|Gln|Glu|Val|Lys|Phe<br>55|Asp|Met|Tyr|Ala|Tyr<br>60|Ser|Ser|Gly|Gly|
|Asp<br>65|Asp|Ser|Lys|Tyr|Pro<br>70|Val|Thr|Leu|Lys|Ile<br>75|Ser|Asp|Ser|Gln|Leu<br>80|
|Phe|Val|Ser|Ala|Gln<br>85|Gly|Glu|Asp|Gln|Pro<br>90|Val|Leu|Leu|Lys|Glu<br>95|Leu|
|Pro|Glu|Thr|Pro<br>100|Lys|Leu|Ile|Thr|Gly<br>105|Ser|Glu|Thr|Asp|Leu<br>110|Ile|Phe|
|Phe|Trp|Lys<br>115|Ser|Ile|Asn|Ser|Lys<br>120|Asn|Tyr|Phe|Thr|Ser<br>125|Ala|Ala|Tyr|
|Pro|Glu<br>130|Leu|Phe|Ile|Ala|Thr<br>135|Lys|Glu|Gln|Ser|Arg<br>140|Val|His|Leu|Ala|
|Arg<br>145|Gly|Leu|Pro|Ser|Met<br>150|Thr|Asp|Phe|Gln|Ile<br>155|Ser| | | | |

(2) INFORMATION FOR SEQ ID NO:4:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 20
        (D) OTHER INFORMATION: /note="methionine sulfoxide"

(xi) SEQUENCE DESCRIPTION: SEQ ID NO:4:

| | | | | | | | | | | | | | | |
|---|---|---|---|---|---|---|---|---|---|---|---|---|---|---|
|Ser<br>1|Gln|Glu|Pro|Pro<br>5|Ile|Ser|Leu|Asp|Leu<br>10|Thr|Phe|His|Leu|Leu<br>15|Arg|
|Glu|Val|Leu|Glu<br>20|Xaa|Thr|Lys|Ala|Asp<br>25|Gln|Leu|Ala|Gln|Gln<br>30|Ala|His|
|Ser|Asn|Arg<br>35|Lys|Leu|Leu|Asp|Ile<br>40|Ala| | | | | | | |

I claim:

1. A process for the conjugation of a functionally useful group to a peptide comprising
    (a) generating an aldehyde by oxidation of a 2-hydroxyethylamine structure, said 2 hydroxyethylamine structure being part of a hydroxylysine residue which is inserted into a synthetic peptide;
    (b) reacting said aldehyde generated in step (a) with a reagent containing a functionally useful group.

2. The process of claim 1 wherein said reagent is a hydrazide.

3. The process of claim 1 wherein the oxidation of step (a) is periodate oxidation.

4. The process of claim 1 wherein said functional group is biotin.

5. The process of claim 1 wherein said functional group is lucifer yellow.

6. The process of claim 1 wherein said functional group is a chromophore.

7. The process of claim 1 wherein said functional group contains a radionuclide.

8. The process of claim 1 wherein said functional group is a fluorescent label.

9. The process of claim 1 wherein said functional group is a drug.

10. The process of claim 9 wherein said drug is a cytotoxic agent.

11. A peptide conjugate having the structure P1—NH—CH—CO—P2 wherein R is a group with useful functional properties and P1 and P2 respectively represent the remainder of the peptide sequence of the amino terminus and carboxy terminus respectively.

* * * * *